(12) United States Patent
Liu et al.

(10) Patent No.: US 11,535,509 B2
(45) Date of Patent: Dec. 27, 2022

(54) SEMICONDUCTOR PACKAGE STRUCTURE AND METHOD FOR MANUFACTURING THE SAME

(71) Applicant: Advanced Semiconductor Engineering, Inc., Kaohsiung (TW)

(72) Inventors: Wei-Wei Liu, Kaohsiung (TW); Huei-Siang Wong, Kaohsiung (TW); Lu-Ming Lai, Kaohsiung (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 270 days.

(21) Appl. No.: 16/685,902

(22) Filed: Nov. 15, 2019

(65) Prior Publication Data
US 2021/0147219 A1 May 20, 2021

(51) Int. Cl.
*B81B 7/00* (2006.01)
*B81C 1/00* (2006.01)
*G01N 33/00* (2006.01)

(52) U.S. Cl.
CPC ........ *B81B 7/0061* (2013.01); *B81C 1/00309* (2013.01); *B81B 2201/0214* (2013.01); *B81B 2201/10* (2013.01); *B81B 2203/0315* (2013.01); *B81B 2207/098* (2013.01); *B81C 2201/0132* (2013.01); *G01N 33/004* (2013.01)

(58) Field of Classification Search
CPC .......... B81B 7/0061; B81B 2201/0214; B81B 2201/10; B81B 2203/0315; B81B 2207/098; B81C 1/00309; B81C 2201/0132; G01N 33/004; H01L 23/3157; H01L 23/66
See application file for complete search history.

(56) References Cited

U.S. PATENT DOCUMENTS

| | | | |
|---|---|---|---|
| 7,791,181 B2 * | 9/2010 | Chen | G01L 19/141 257/676 |
| 8,433,084 B2 * | 4/2013 | Conti | H04R 19/04 381/174 |
| 9,082,681 B2 | 7/2015 | Neel et al. | |
| 10,118,816 B2 | 11/2018 | Elian et al. | |
| 2019/0135614 A1 * | 5/2019 | Kierse | G01N 33/0009 |

* cited by examiner

*Primary Examiner* — Dale E Page
*Assistant Examiner* — Quovaunda Jefferson
(74) *Attorney, Agent, or Firm* — Foley & Lardner LLP

(57) ABSTRACT

A semiconductor package structure includes an electronic device having a first surface and an exposed region adjacent to the first surface; a dam disposed on the first surface and surrounding the exposed region of the electronic device; and a filter structure disposed on the dam.

13 Claims, 17 Drawing Sheets

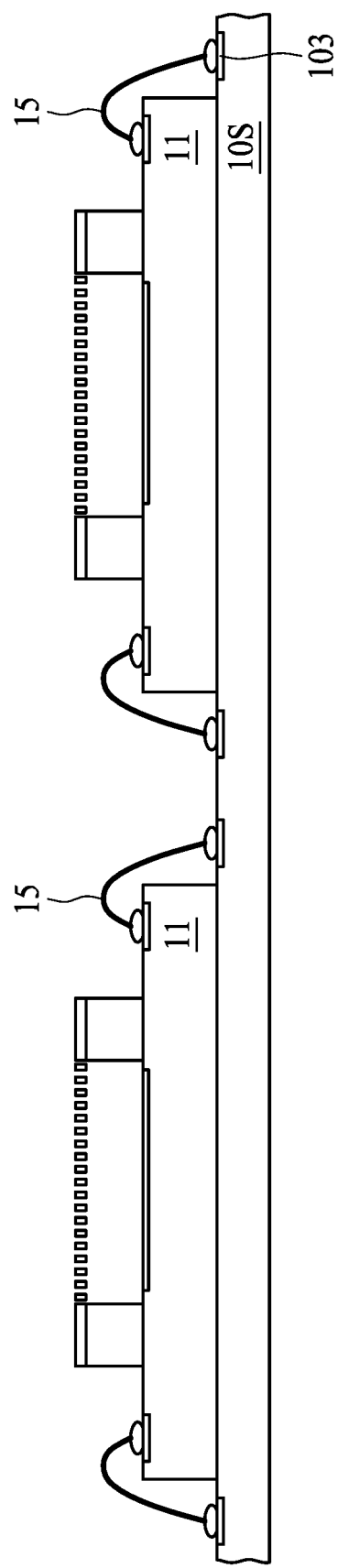

SEMICONDUCTOR PACKAGE STRUCTURE AND METHOD FOR MANUFACTURING THE SAME

BACKGROUND

1. Technical Field

The present disclosure relates to semiconductor package structures.

2. Description of the Related Art

A semiconductor package structure can include a semiconductor device disposed on a carrier. The semiconductor device can sense an environmental condition. As a result, a portion of the semiconductor device (e.g. the working area) should be exposed to the environment (or air) to function or work.

However, some substances, which can access the exposed portion of the semiconductor device, may adversely affect performance of the semiconductor package structure.

SUMMARY

In some embodiments, the present disclosure provides a semiconductor package structure, which includes an electronic device having a first surface and an exposed region adjacent to the first surface; a dam disposed on the first surface and surrounding the exposed region of the electronic device; and a filter structure disposed on the dam.

In some embodiments, the present disclosure provides a semiconductor package structure, which includes an electronic device having an exposed region adjacent to a first surface; and a filter structure disposed on the exposed region of the electronic device.

In some embodiments, the present disclosure provides a method for manufacturing a semiconductor package structure, the method includes patterning a passivation layer over a first surface of a wafer to form a number of dams; disposing a first film on the number of dams; and patterning the first film.

BRIEF DESCRIPTION OF THE DRAWINGS

Aspects of the present disclosure are readily understood from the following detailed description when read with the accompanying figures. It should be noted that various features may not be drawn to scale. In fact, the dimensions of the various features may be arbitrarily increased or reduced for clarity of discussion.

FIG. 6A, FIG. 6B, FIG. 6C, FIG. 6D, FIG. 6E, FIG. 6F, FIG. 6G, FIG. 6H and FIG. 6I illustrates cross sections of a semiconductor package structure during various manufacturing operations, according to some embodiments of the present disclosure.

DETAILED DESCRIPTION

Figure 1:
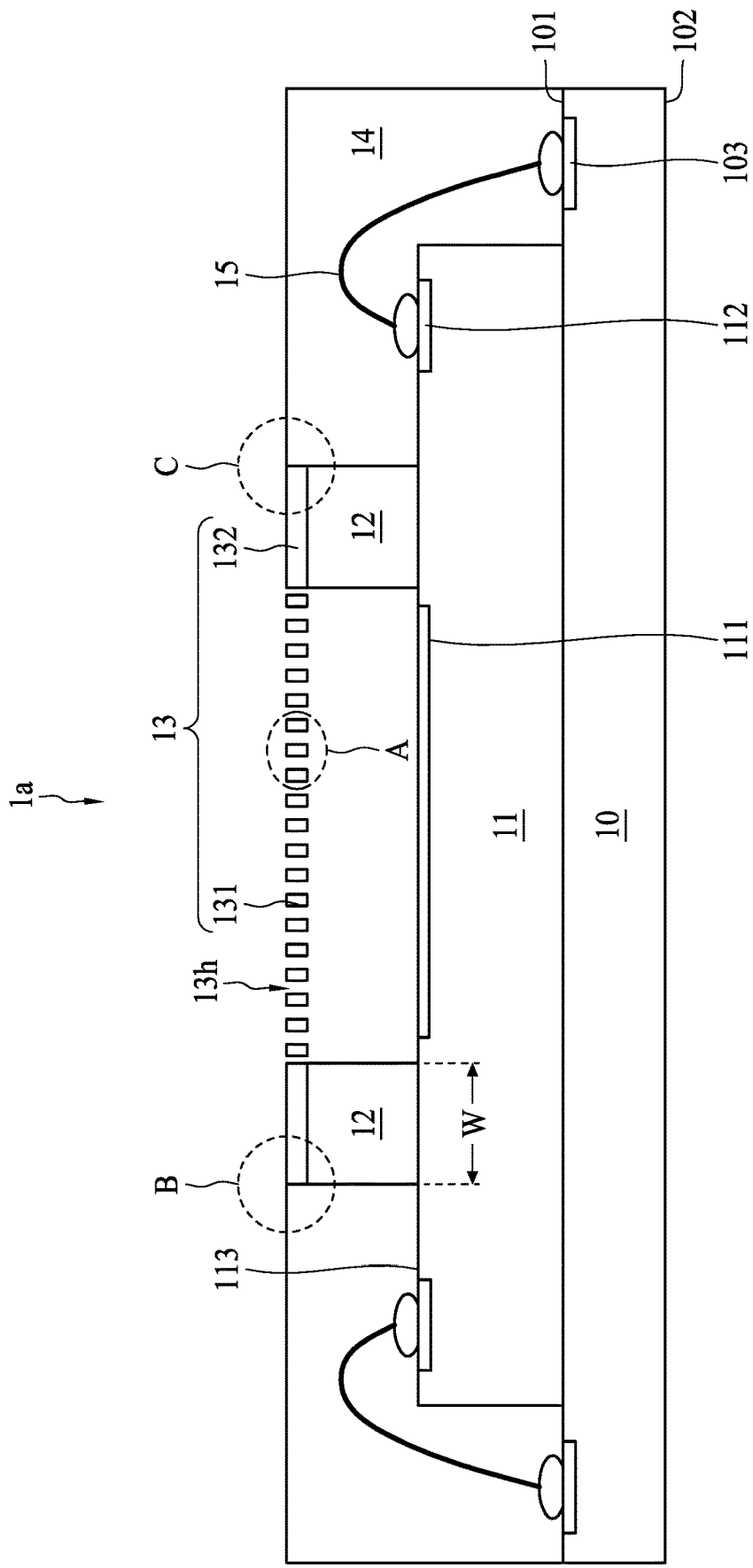
FIG. 1 illustrates a cross-sectional view of a semiconductor package structure, according to some embodiments of the present disclosure.

Common reference numerals are used throughout the drawings and the detailed description to indicate the same or similar components. Embodiments of the present disclosure will be readily understood from the following detailed description taken in conjunction with the accompanying drawings.

Spatial descriptions, such as "above," "below," "up," "left," "right," "down," "top," "bottom," "vertical," "horizontal," "side," "higher," "lower," "upper," "over," "under," and so forth, are specified with respect to a certain component or group of components, or a certain plane of a component or group of components, for the orientation of the component(s) as shown in the associated figure. It should be understood that the spatial descriptions used herein are for purposes of illustration only, and that practical implementations of the structures described herein can be spatially arranged in any orientation or manner, provided that the merits of embodiments of this disclosure are not deviated from by such arrangement.

Active region of a semiconductor device or an electronic device (e.g. a Micro Electro Mechanical System (MEMS) die or chip) can be sensitive to some substances. For example, a gas sensor or detector can be designed to be sensitive to gas which may include, for example but is not limited to, carbon dioxide, carbon monoxide, methane, or other substance(s).

During manufacturing operations in packaging the semiconductor device, an open cavity molding should be applied to expose the active region of the semiconductor device. A dam structure may be applied to surround the active region prior to the molding operation so that the molding tool may not directly abut the active region and at the same time, prevent the molding compound from entering the predetermined open cavity.

Although the dam, which can have an opening to expose the active region of the semiconductor device, can allow substance(s) of interest to enter the cavity, however, the dam may also allow unwanted substance(s) (e.g. water vapor, liquid water, other particle(s)) to enter the cavity or to reach the active region of the semiconductor device, which can adversely affect performance of the semiconductor device structure.

Present disclosure provides a filter structure to allow substances or particles having certain size(s) to pass through.

FIG. 1 illustrates a cross-sectional view of a semiconductor package structure, according to some embodiments of the present disclosure.

Referring to FIG. 1, the semiconductor package structure 1a can include a carrier 10, an electronic device 11 (or semiconductor device 11), a dam 12, a filter structure 13, an encapsulant 14 and conductive wires 15.

The carrier 10 can include, for example but is not limited to, a lead frame, a substrate, an interposer, or the like. The carrier 10 can have a redistribution layer (RDL) structure, which may include passivation layer and patterned conductive layer. The carrier 10 can have circuitry, which can include conductive trace(s), via(s), pad(s), etc. (not shown in FIG. 1). The carrier 10 can have a single-layer structure. The carrier 10 can have a multi-layer structure. The carrier 10 has a surface 101 and another surface 102 opposite the surface 101. The carrier 10 includes some conductive pads 103 adjacent to the surface 101.

The electronic device 11 can include a semiconductor die or semiconductor chip. The electronic device 11 can include, for example but is not limited to, a Micro Electro Mechanical System (MEMS) die or chip. The electronic device 11 can include a sensor die which can be sensitive to some substances. For example, the electronic device 11 can include a gas sensor or detector, which is sensitive to, for example but is not limited to, carbon dioxide, carbon monoxide, methane, or other substance(s).

The electronic device 11 has some conductive pads 112. Although the electronic device 11 shown in FIG. 1 is a wire-bond type structure, however, it is contemplated that the semiconductor package structure 1a can include a flip-chip type electronic device in some other embodiments of the present disclosure. The electronic device 11 has a surface 113. The electronic device 11 can have a circuit adjacent to the surface 113. The electronic device 11 can have an active region or sensing region 111 adjacent to the surface 113. The region 111 can be exposed to air within the cavity formed above the electronic device 11. The electronic device 11 can have a width less than 1 millimeter (mm).

The electronic device 11 is disposed on the carrier 10. The electronic device 11 can be attached to the carrier 10 by an adhesive layer (not shown in FIG. 1), which may include, for example but is not limited to, glue, gel, film or other types of adhesive. The electronic device 11 can be electrically connected to the carrier 10 by conductive wires 15. The conductive wire 15 can be bonded to the conductive pad 103. The conductive wire 15 can be bonded to the conductive pad 112.

The region 111 can be sensitive to, for example but is not limited to, carbon dioxide, carbon monoxide, methane, or other substance(s). The region 111 can detect, for example but is not limited to, molecules or particles having an average size less than approximately 2.8 micrometer ($\mu m$).

The region 111 can be susceptible to other substance(s), for example, water or water molecule. The region 111 can be susceptible to molecules or particles having an average size equal to or greater than approximately 2.8 $\mu m$. An average dimension of water molecules can be equal to or greater than approximately 2.8 $\mu m$. Certain molecules or particles, for example, water molecules, can hamper or hinder operation of the region 111.

The dam 12 can include, for example but is not limited to, epoxy-based material, polymeric material, or other suitable material(s). The dam 12 can have a circular shape from a top view perspective. The dam 12 can have a circular-like shape from a top view perspective. The dam 12 can have a rectangular shape from a top view perspective. The dam 12 can have a rectangular-like shape from a top view perspective. The shape of the dam 12, from a top view perspective, can be varied of design interest.

The dam 12 is disposed on the surface 113 of the electronic device 11. The dam 12 can surround the region 111 of the electronic device 11. The dam 12 can enclose the region 111 of the electronic device 11. The dam 12 can have a width W of approximately 100 $\mu m$. The dam 12 can have a thickness or height from approximately 60 $\mu m$ to approximately 100 $\mu m$. The dam 12 can define a space or cavity having a width from approximately 200 $\mu m$ to approximately 300 $\mu m$. Dimension of the dam 12 can be varied of design interest. An upper surface (e.g. top surface) of the dam 12 can be disposed at an elevation equal to a top portion (not denoted in FIG. 1) of the conductive wire 15. An upper surface (e.g. top surface) of the dam 12 can be disposed at an elevation greater than a top portion (not denoted in FIG. 1) of the conductive wire 15. An upper surface (e.g. top surface) of the dam 12 can be higher than a top point (not denoted in FIG. 1) of the conductive wire 15. An upper surface (e.g. top surface) of the dam 12 can be elevationally same to a top point (not denoted in FIG. 1) of the conductive wire 15.

The dam 12 can be spaced apart from the region 111. It is contemplated that the inner side surface of the dam 12 can be aligned or coplanar with a side, boundary or edge of the region 111 in some other embodiments of the present disclosure. It is contemplated that the dam 12 can cover or overlap the region 111 in some other embodiments of the present disclosure. It is contemplated that the dam 12 can cover or overlap part of the region 111 in some other embodiments of the present disclosure. It is contemplated that the dam 12 can cover or overlap periphery or edge of the region 111 in some other embodiments of the present disclosure.

The filter structure 13 can include a portion 131 and another portion 132. The portion 132 can surround the portion 131. The portion 132 can enclose the portion 131. The portion 132 can be supported by the dam 12. The portion 132 can be in direct contact with the dam 12. The portion 132 can be in direct contact with the encapsulant 14.

The filter structure 13 can have a width less than the electronic device 11. The filter structure 13 can have a surface area less than the electronic device 11.

The filter structure 13 can have a thickness of approximately 10 $\mu m$. The portion 131 can have a mesh or grid from a top view perspective. The portion 131 can define some though holes 13h. The though hole 13 can have a width between approximately 1.0 $\mu m$ and approximately 2.8 $\mu m$. The though hole 13 can penetrate the portion 131. The though hole 13 can include, for example but is not limited to, cylindrical, cylinder-like, cone, cone-like, or other shape(s) or contour(s). Molecules or particles, which have size or width less than approximately 2.8 $\mu m$, can pass the though holes 13. Molecules or particles, which have size or width equal to or greater than approximately 2.8 $\mu m$, cannot pass the though holes 13. In other words, molecules which have size or width less than approximately 2.8 $\mu m$ can move from external environment into the cavity defined by the dam 12, and arrive at the region 111. Molecules which have size or width equal to or greater than approximately 2.8 $\mu m$ can be blocked by the filter structure 13 from the region 111. The semiconductor package structure 1a can be waterproof while performing sensing or detection function as well.

The encapsulant 14 can encapsulate the carrier 10. The encapsulant 14 can encapsulate the electronic device 11. The encapsulant 14 can encapsulate the surface 113 of the electronic device 11. The encapsulant 14 can encapsulate the dam 12. The encapsulant 14 can encapsulate the filter structure 13. The encapsulant 14 can encapsulate the portion 132 of the filter structure 13. The encapsulant 14 can surround the dam 12. The encapsulant 14 can surround the filter structure 13. The encapsulant 14 can enclose the dam 12. The encapsulant 14 can enclose the filter structure 13. The encapsulant 14 can be in direct contact with the dam 12. The encapsulant 14 can be in direct contact with the filter structure 13. The encapsulant 14 can be in direct contact with the portion 132 of the filter structure 13. The dam 12 can be retracted from a top surface of the encapsulant 14. The dam 12 can have a top surface lower than a top surface of the encapsulant 14.

The encapsulant 14 can include epoxy-base material. The encapsulant 14 can include fillers or particles. The encapsulant 14 can include molding compound.

Figure 1B:
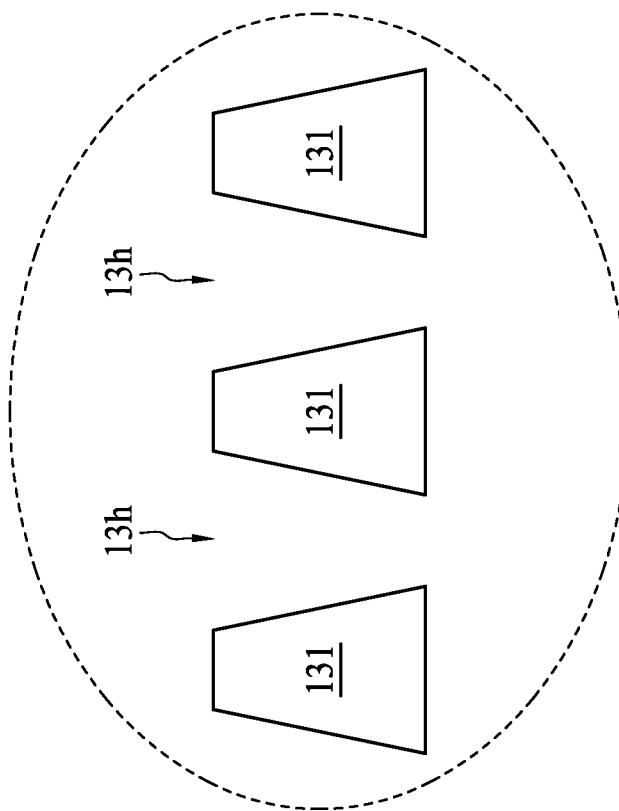
FIG. 1B illustrates an enlarged view of the structure in the dotted circle A as shown in FIG. 1.
Figure 1A:
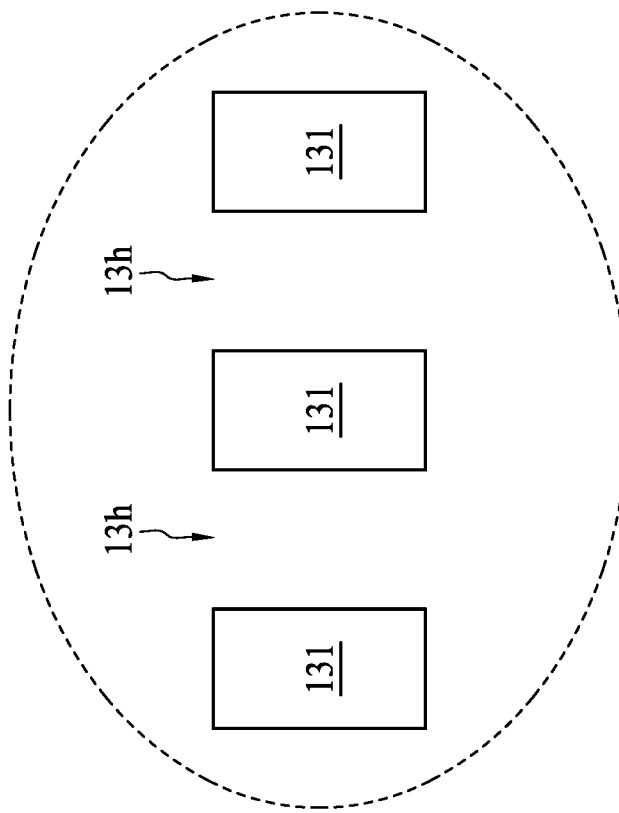
FIG. 1A illustrates an enlarged view of the structure in the dotted circle A as shown in FIG. 1.

FIG. 1A illustrates an enlarged view of the structure in the dotted circle A as shown in FIG. 1.

Referring to FIG. 1A, the portion 131 of the filter structure 13 can define some through holes 13h having a constant width.

FIG. 1B illustrates an enlarged view of the structure in the dotted circle A as shown in FIG. 1.

Referring to FIG. 1B, the portion 131 of the filter structure 13 can define some tapered through holes 13h.

Figure 1D:
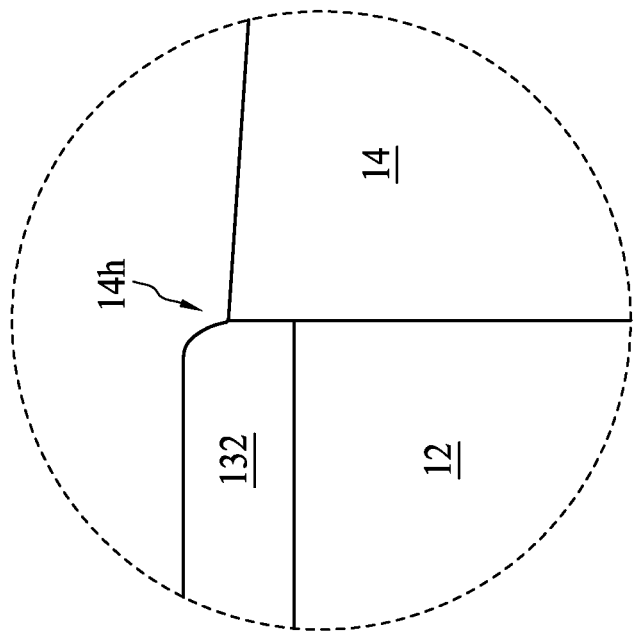
FIG. 1D illustrates an enlarged view of the structure in the dotted circle C as shown in FIG. 1.
Figure 1C:
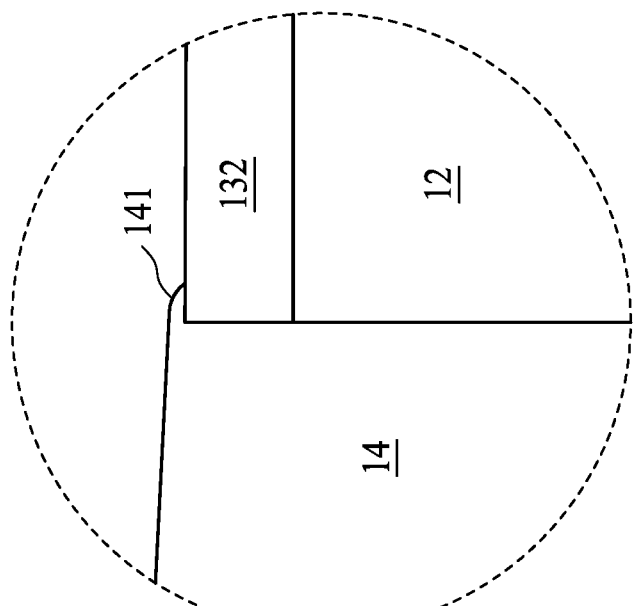
FIG. 1C illustrates an enlarged view of the structure in the dotted circle B as shown in FIG. 1.

FIG. 1C illustrates an enlarged view of the structure in the dotted circle B as shown in FIG. 1.

Referring to FIG. 1C, the encapsulant 14 can have an extension 141. The extension 141 can cover the portion 132 of the filter structure 13. The extension 141 can cover an edge or periphery of the portion 132 of the filter structure 13. The encapsulant 14 can have a slant surface. The encapsulant 14 can have a portion having a relatively great thickness away from the portion 132 of the filter structure 13. The encapsulant 14 can have a portion having a relatively less thickness adjacent to the portion 132 of the filter structure 13. The encapsulant 14 can have a top surface higher than a top surface of the portion 132 of the filter structure 13.

FIG. 1D illustrates an enlarged view of the structure in the dotted circle C as shown in FIG. 1.

Referring to FIG. 1D, a hole 14h (or recess or cavity) can be formed in the encapsulant 14. The hole 14h can be adjacent to the portion 132 of the filter structure 13. The hole 14h can expose the portion 132 of the filter structure 13. The hole 14h can expose a side surface of the portion 132 of the filter structure 13. The hole 14h can expose a part of a side surface of the portion 132 of the filter structure 13. The encapsulant 14 can have a slant surface. The encapsulant 14 can have a portion having a relatively less thickness away from the portion 132 of the filter structure 13. The encapsulant 14 can have a portion having a relatively great thickness adjacent to the portion 132 of the filter structure 13. The encapsulant 14 can have a top surface lower than a top surface of the portion 132 of the filter structure 13.

Figure 2:
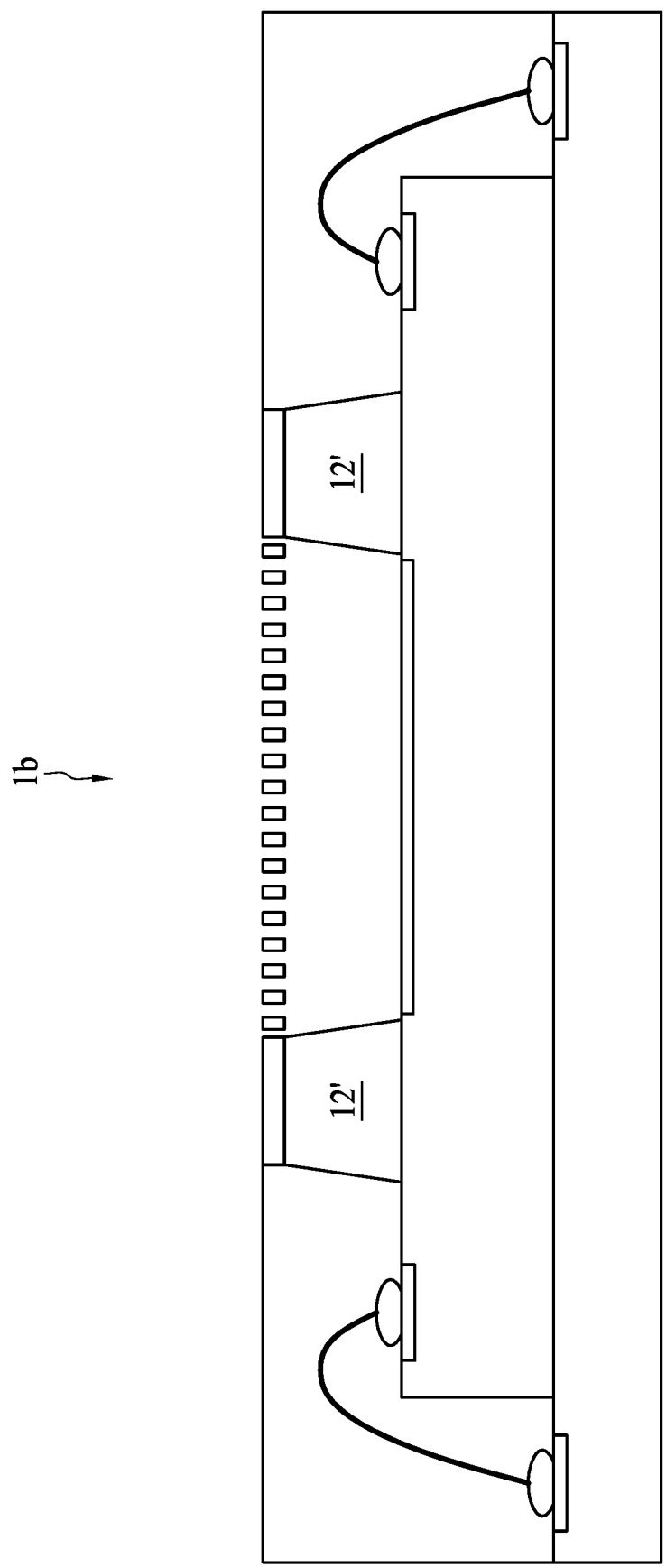
FIG. 2 illustrates a cross-sectional view of a semiconductor package structure, according to some other embodiments of the present disclosure.

FIG. 2 illustrates a cross-sectional view of a semiconductor package structure, according to some other embodiments of the present disclosure.

Referring to FIG. 2, the semiconductor package structure 1b is similar to the semiconductor package structure 1a as described and illustrated with reference to FIG. 1, except that the dam 12 of the semiconductor package structure 1a is replaced by the dam 12' to form the semiconductor package structure 1b.

The dam 12' can have a tapered profile from a cross-section view perspective. The dam 12' can have a relatively wide base. The dam 12' can include a lower surface having a relatively greater surface area. The dam 12' can include an upper surface having a relatively less surface area. The dam 12' can have a lower portion having a width greater than an upper portion. The dam' 12' can provide a reinforced support for the filter structure 13. The inner side surface of base of the dam 12' can be aligned or coplanar with a side, boundary or edge of the region 111.

Figure 3:
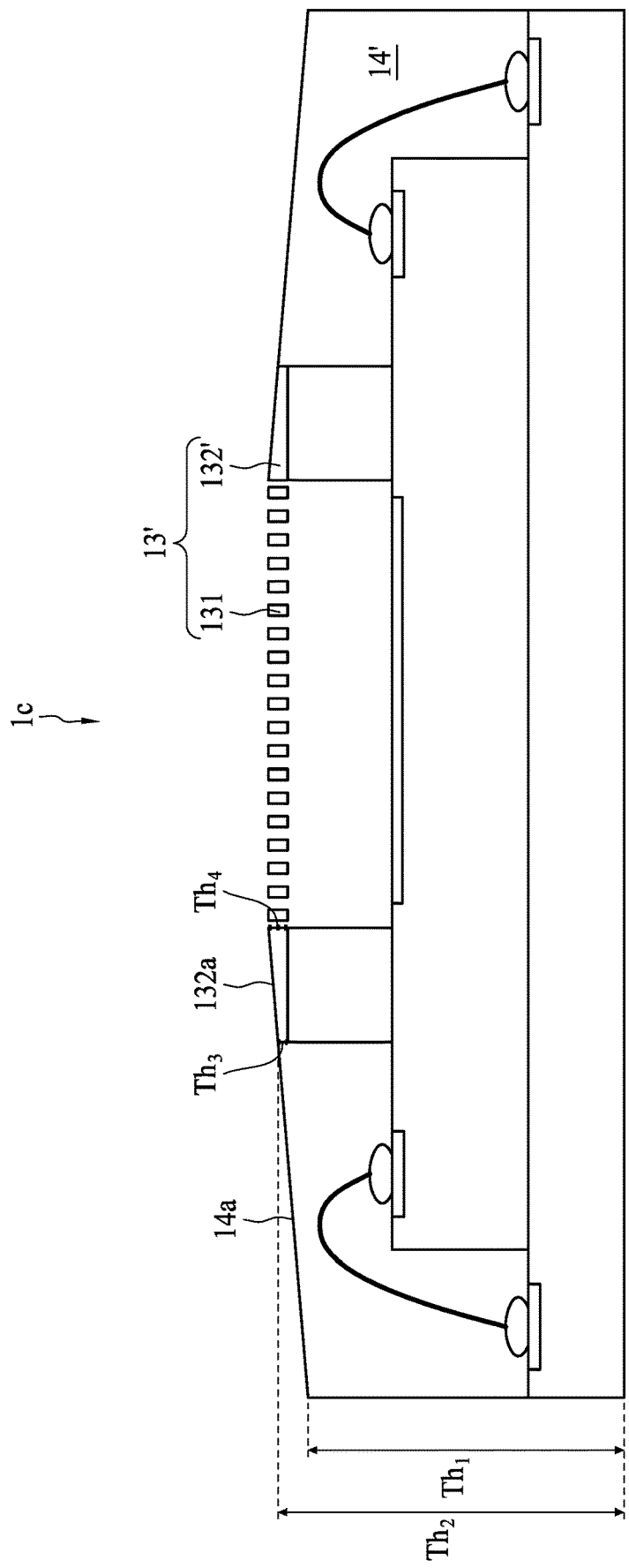
FIG. 3 illustrates a cross-sectional view of a semiconductor package structure, according to some other embodiments of the present disclosure.

FIG. 3 illustrates a cross-sectional view of a semiconductor package structure, according to some other embodiments of the present disclosure.

Referring to FIG. 3, the semiconductor package structure 1c is similar to the semiconductor package structure 1a as described and illustrated with reference to FIG. 1, except that the encapsulant 14 and the filter structure 13 of the semiconductor package structure 1a are replaced by the encapsulant 14' and the filter structure 13' to form the semiconductor package structure 1c.

The encapsulant 14' is similar to the encapsulant 14 as described and illustrated with reference to FIG. 1, except that the encapsulant 14' has a slant surface 14a. The encapsulant 14' can have a thickness $Th_2$ adjacent to the dam 12 and another thickness $Th_1$ away from the dam 12, and the thickness $Th_2$ can be greater than the thickness $Th_1$. The encapsulant 14' can have a relatively central portion which is relatively great in thickness. The encapsulant 14' can have a relatively periphery portion which is relatively less in thickness.

The filter structure 13' is similar to the filter structure 13 as described and illustrated with reference to FIG. 1, except that the portion 132 of the filter structure 13 is replaced by the portion 132' to form the filter structure 13'. The portion 132' of the filter structure 13' is tapered from a cross sectional perspective. The portion 132' of the filter structure 13' can have a thickness $Th_4$ adjacent to the portion 131 of the filter structure 13' and another thickness $Th_3$ away from the portion 131 of the filter structure 13', and the thickness $Th_4$ is greater than the thickness $Th_3$. The filter structure 13' can have a relatively central portion which is relatively great in thickness. The filter structure 13' can have a relatively periphery portion which is relatively less in thickness. The portion 132' of the filter structure 13' can have a slant surface 132a.

Figure 4:
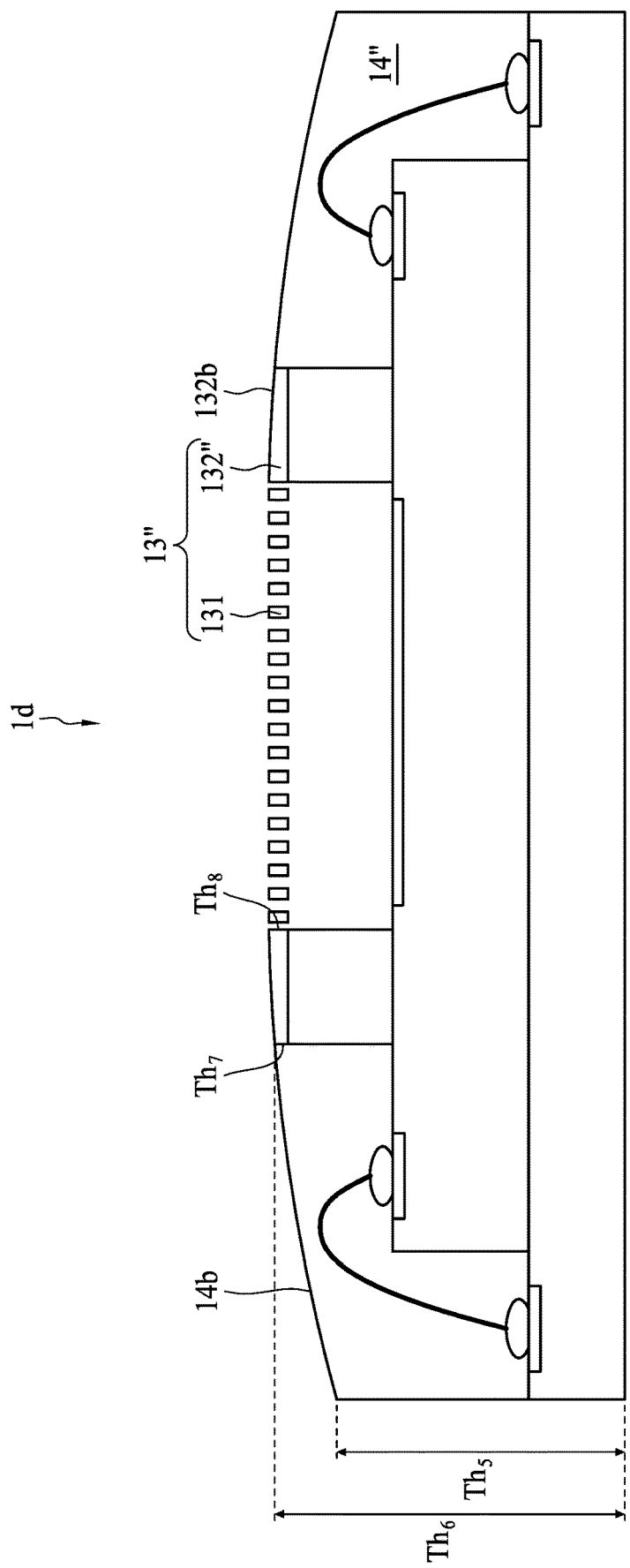
FIG. 4 illustrates a cross-sectional view of a semiconductor package structure, according to some other embodiments of the present disclosure.

FIG. 4 illustrates a cross-sectional view of a semiconductor package structure, according to some other embodiments of the present disclosure.

Referring to FIG. 4, the semiconductor package structure 1d is similar to the semiconductor package structure 1a as described and illustrated with reference to FIG. 1, except that the encapsulant 14 and the filter structure 13 of the semiconductor package structure 1a are replaced by the encapsulant 14" and the filter structure 13" to form the semiconductor package structure 1d.

The encapsulant 14" is similar to the encapsulant 14 as described and illustrated with reference to FIG. 1, except that the encapsulant 14" has a curve surface 14b. The encapsulant 14" can have a thickness $Th_6$ adjacent to the dam 12 and another thickness $Th_5$ away from the dam 12, and the thickness $Th_6$ can be greater than the thickness $Th_5$. The encapsulant 14" can have a relatively central portion which is relatively great in thickness. The encapsulant 14" can have a relatively periphery portion which is relatively less in thickness.

The filter structure 13" is similar to the filter structure 13 as described and illustrated with reference to FIG. 1, except that the portion 132 of the filter structure 13 is replaced by the portion 132" to form the filter structure 13". The portion 132" of the filter structure 13" is tapered from a cross sectional perspective. The portion 132" of the filter structure 13" can have a thickness $Th_8$ adjacent to the portion 131 of the filter structure 13" and another thickness $Th_7$ away from the portion 131 of the filter structure 13", and the thickness Th$_8$ is greater than the thickness Th$_7$. The filter structure 13" can have a relatively central portion which is relatively great in thickness. The filter structure 13" can have a relatively periphery portion which is relatively less in thickness. The portion 132" of the filter structure 13" can have a curve surface 132b.

Figure 5A:
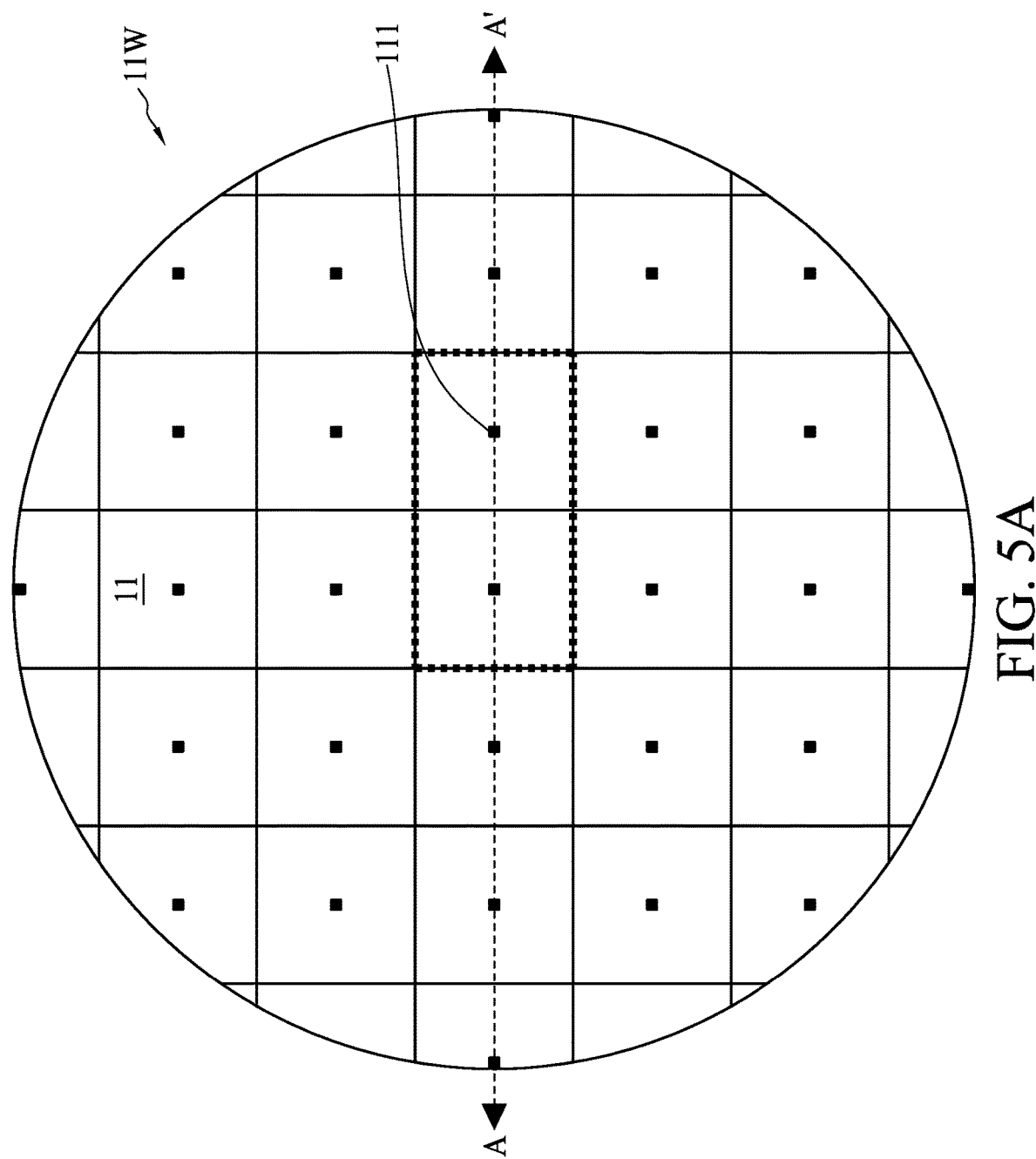
FIG. 5A and FIG. 5B illustrates a top view of a semiconductor package structure during various manufacturing operations, according to some embodiments of the present disclosure.
Figure 5B:
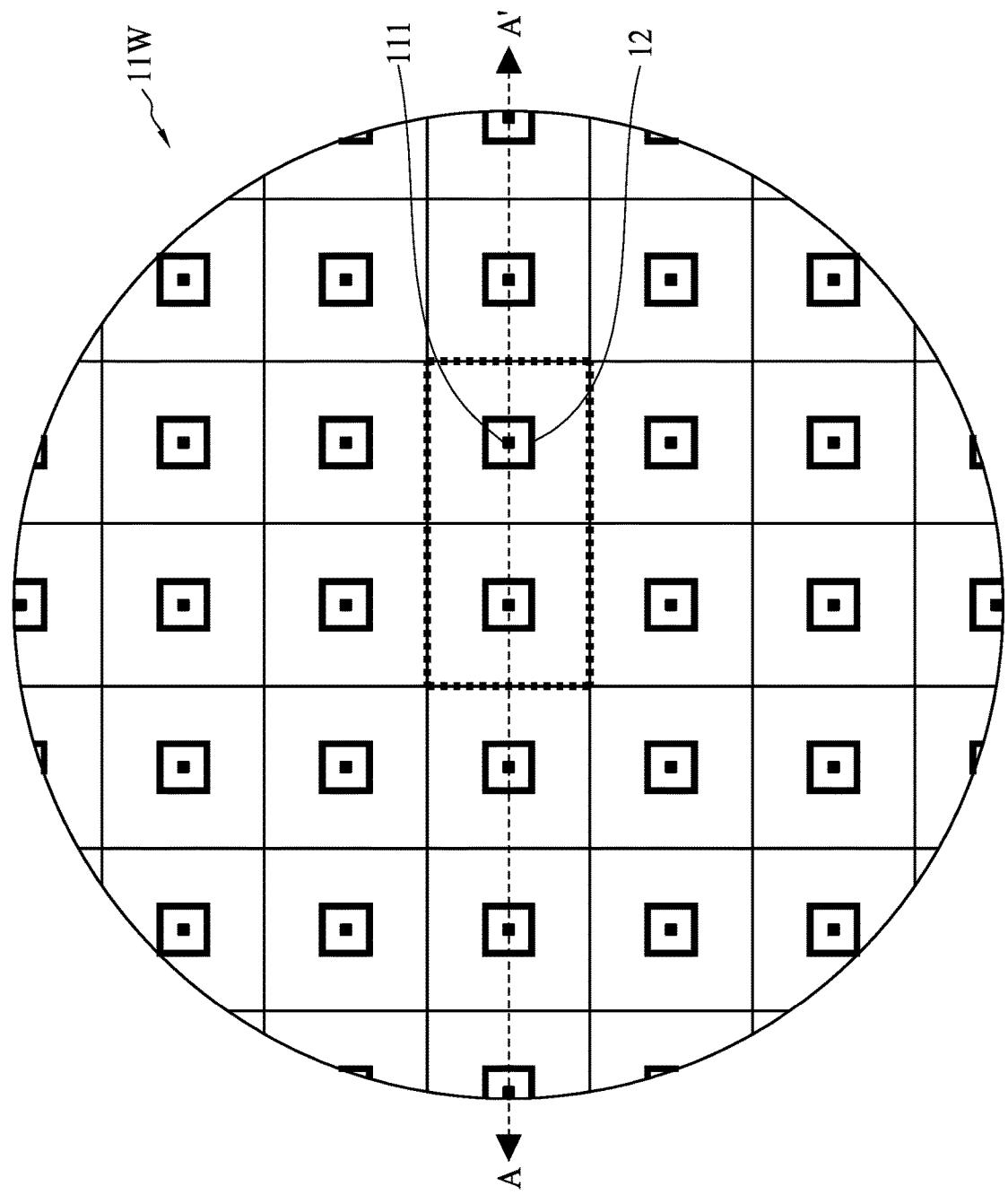

FIG. 5A and FIG. 5B illustrates a top view of a semiconductor package structure during various manufacturing operations, according to some embodiments of the present disclosure.

Referring to FIG. 5A, a semiconductor wafer 11W is provided. The semiconductor wafer 11W can include some semiconductor devices 11 or electronic devices 11. Each of the electronic device 11 can have an active region 111. Although the active region 111 is disposed adjacent to the center of the electronic device 11, however, it is contemplated that the active region 111 can be disposed at other position in the electronic device 11.

Referring to FIG. 5B, a dam 12 is formed on each of the electronic device 11 to surround or enclose the active region 111. Although the dam 12 as shown in FIG. 5B has a rectangle, square, rectangle-like shape, however, it is contemplated that the dam 12 can have a circle, triangle, or other shape(s). The dam 12 can have a ring structure to enclose the active region 111.

FIG. 6A, FIG. 6B, FIG. 6C, FIG. 6D, FIG. 6E, FIG. 6F, FIG. 6G, FIG. 6H and FIG. 6I illustrates cross sections of a semiconductor package structure during various manufacturing operations, according to some embodiments of the present disclosure.

Figure 6A:
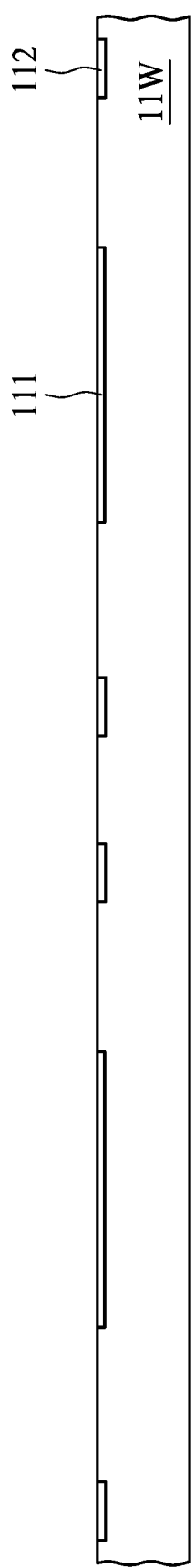

Referring to FIG. 6A, which illustrates a cross section of the structure in the dotted box across line AA' as shown in FIG. 5A. The semiconductor wafer 11W is provided. The semiconductor wafer 11W can include some electronic devices 11. Each of the electronic device 11 can have an active region 111 and some conductive pads 112.

Figure 6B:
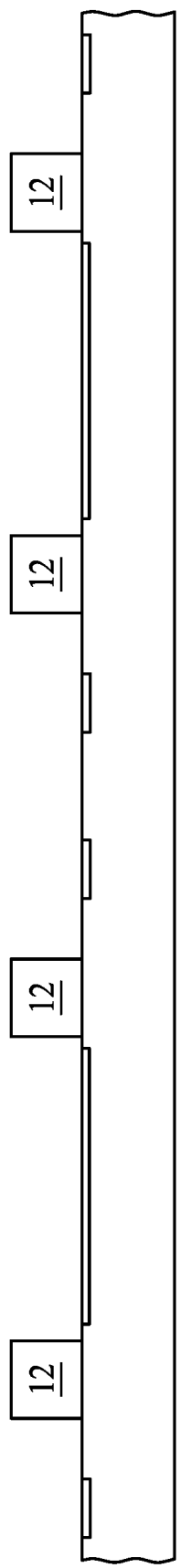

Referring to FIG. 6B, which illustrates a cross section of the structure in the dotted box across line AA' as shown in FIG. 5B. The dam 12 is formed to surround or enclose the active region 111. Although the dam 12 as shown in FIG. 6B has an edge (e.g. inner side surface) spaced apart from the active region 111, however, it is contemplated that the dam 12 can sit on the active region 111 in some other embodiments of the present disclosure. In other words, the dam 12 can be in direct contact with the active region 111.

The dam 12 can be formed by coating technique. The dam 12 can be formed by photolithography technique. For example, a layer of epoxy-based material can be formed on the wafer 11W by spin coating technique. The layer of epoxy-based material formed by coating technique can have a relatively great thickness adjacent to the periphery. The layer of epoxy-based material formed by coating technique can be relatively cost effective. For example, a layer of epoxy-based material can be formed on the wafer 11W by attaching a dry film (of epoxy-based material) onto the wafer 11W. The layer of epoxy-based material formed from dry film can have a relatively constant thickness.

The layer of epoxy-based material can then be patterned by, for example but is not limited to, exposure technique, developing technique and other suitable technique(s), to form a patterned layer of epoxy-based material. The patterned layer of epoxy-based material can then be hardened, solidified or cured by, for example but is not limited to, heat, radiation or other suitable technique(s) to form the dam 12 as described and illustrated with reference to FIG. 1, FIG. 3 and FIG. 4.

It is contemplated that parameter(s) (e.g. optical parameter(s)) can be varied to form the dam 12' as described and illustrated with reference to FIG. 2.

Figure 6C:
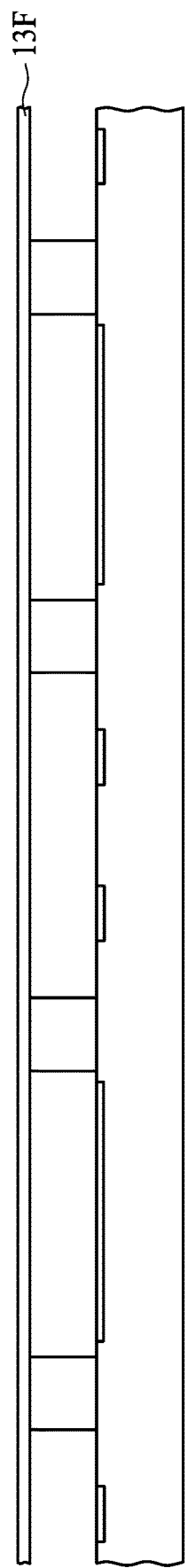

Referring to FIG. 6C, a layer of epoxy-based material 13F can be formed on the dams 12. The layer 13F can include organic material(s). The layer 13F can include a film type structure. The layer 13F can be hardened, solidified or cured by, for example but is not limited to, heat, radiation or other suitable technique(s). The layer 13F can have a thickness of approximately 10 μm. Thickness of the layer 13F can be varied of design interest.

Figure 6D:
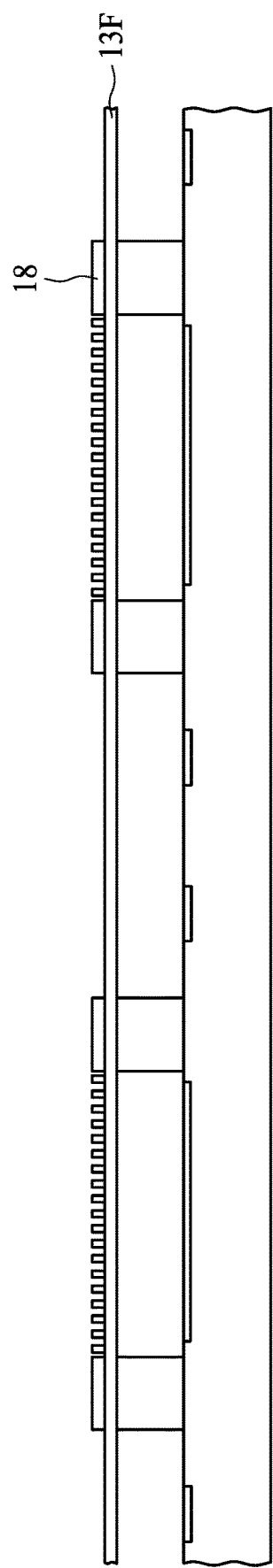

Referring to FIG. 6D, a mask 18 can be formed on the layer 13F. The mask 18 can include organic material(s) (e.g. epoxy-based material), metal, alloy, or other suitable material(s).

For example, a liquid epoxy-based material or film can be formed on the layer 13F. The liquid epoxy-based material can then be patterned by, for example but is not limited to, exposure technique, developing technique and other suitable technique(s), to form a patterned layer of epoxy-based material. The patterned layer of epoxy-based material can then be hardened, solidified or cured by, for example but is not limited to, heat, radiation or other suitable technique(s) to form the mask 18. It is contemplated that the mask 18 can include material(s) which can be resistive to the substance(s) used in the subsequent operation (e.g. deep reactive-ion etching (DRIE) operation).

For example, a metal film can be formed on the layer 13F by sputtering technique. A photoresist (PR) layer can be formed on the metal film by coating technique. The PR layer can then be patterned by, for example but is not limited to, exposure technique, developing technique and other suitable technique(s), to form a patterned PR mask. An etching operation can be performed on the metal film, with the help of the patterned PR mask, to form a metal mask 18.

Figure 6E:
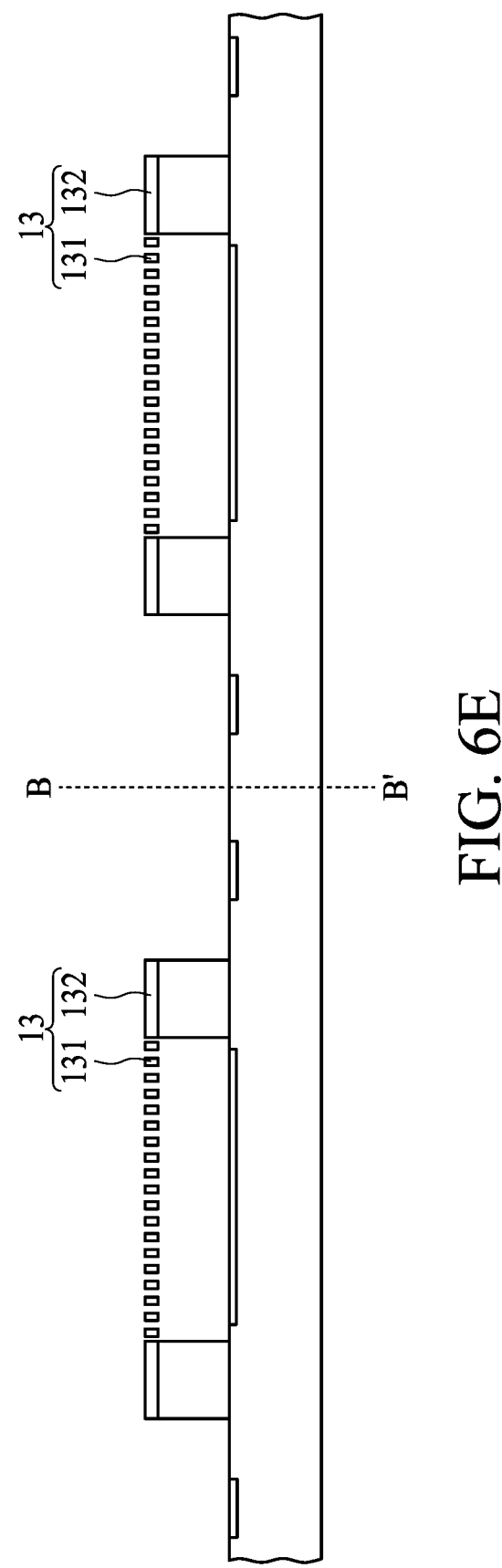

Referring to FIG. 6E, part of the layer 13F is removed to form a filter structure 13. The part of the layer 13F can be removed by etching technique. For example, some portions of the layer 13F, which are not covered or protected by the mask 18 as shown in FIG. 6D, can be removed by dry etching technique (e.g. DRIE technique or ion bombard technique).

The mask 18 including cured epoxy-based material can be used to form a filter structure 13 having a portion 131 as described and illustrated with reference to FIG. 1B. The mask 18 including cured epoxy-based material can be removed by stripping technique. The mask 18 can be removed by stripper for stripping epoxy-based material or photo resist.

The metal mask 18 can be used to form a filter structure 13 having a portion 131 as described and illustrated with reference to FIG. 1A. The metal mask 18 can be removed by stripping technique. The metal mask 18 can be removed by stripper or etchant for metal etching.

Referring to FIG. 6F, a singulation or cutting operation can be performed on the structure along the scribe lines BB' as show in FIG. 6E. Some or all the singulated structures (or units) can be picked and placed on a carrier 10S. The carrier 10S can include a strip or panel of some substrates or substrate units. Each of the singulated structure can be attached to the carrier 10S by adhesive or other suitable bonding material(s). Each of the singulated structure can be electrically connected to the carrier 10S by wire-bonding technique. The conductive wires 15 can be bonded to the singulated structures and the carrier 10S.

Figure 6G:
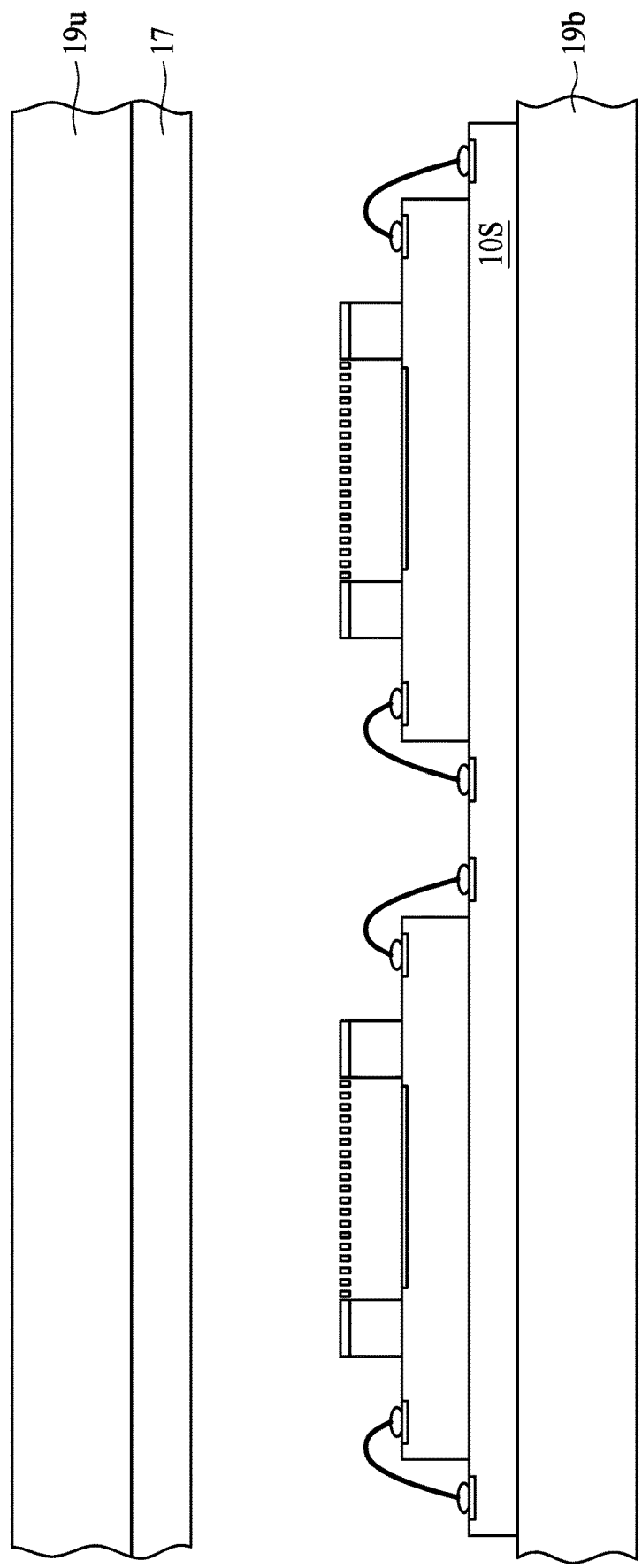

Referring to FIG. 6G, the structure as shown in FIG. 6F can be disposed in a mold tool or mold chase, which can include an upper part 19u and a lower part 19b. A release film 17 can be attached to the upper part 19u of the mold tool. The release film 17 can have a thickness of approximately 50 μm.

Figure 6H:
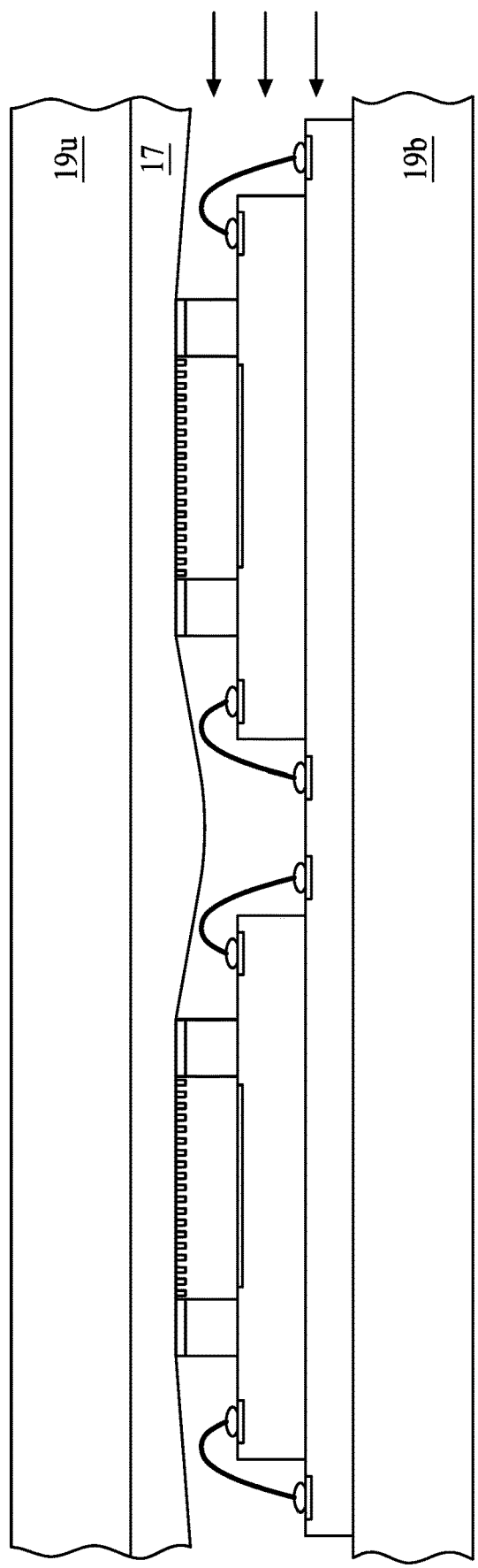

Referring to FIG. 6H, a molding operation (e.g. transfer molding technique) can be performed. During the molding operation, the upper part 19u can be moved toward the lower part 19b with stress and heat. The stress applied on the upper part 19u and the lower part 19b can deform the release film 17. The deformed film 17 can have a relatively great thickness at or adjacent to center. The deformed film 17 can have a relatively less thickness at or adjacent to periphery. The deformed film 17 can have a relatively less thickness at or adjacent to edge. Encapsulant material or mold compound can flow (as indicated by the arrows as shown in FIG. 6H) to encapsulate the structure in the mold tool.

Figure 6I:
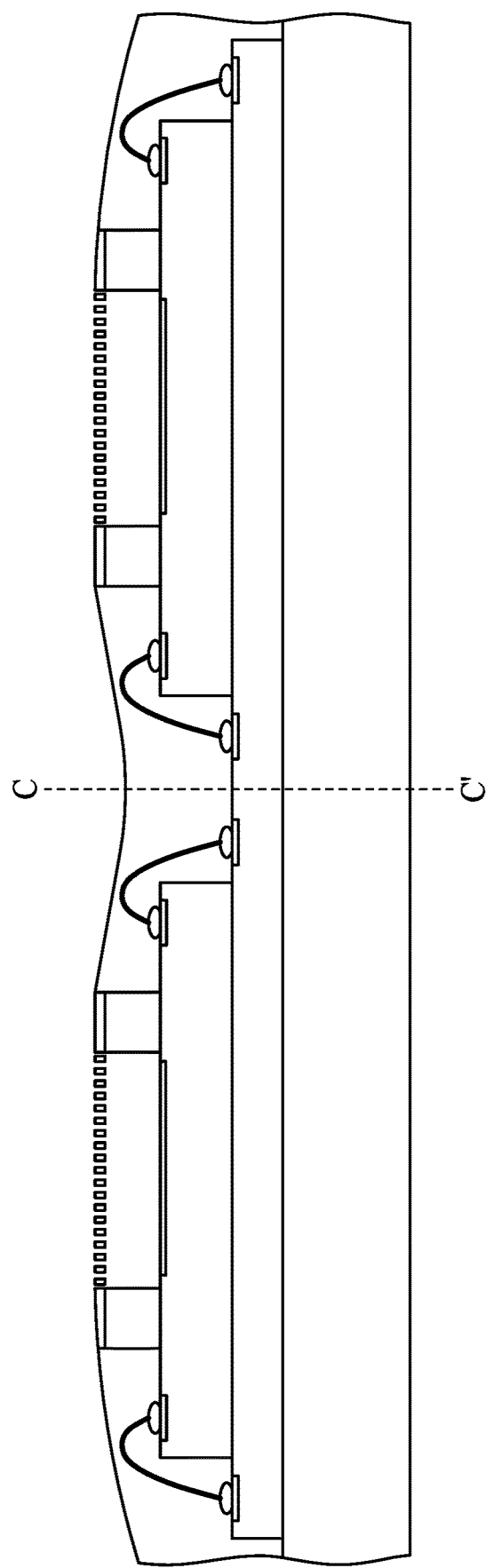

Referring to FIG. 6I, subsequent to the molding operation as shown in FIG. 6H, the molded structure can be removed from the mold tool. A singulation or cutting operation can be performed on the molded structure along the scribe lines CC' as show in FIG. 6I to form some semiconductor package structures 1a, 1b, 1c, or 1d as described and illustrated with reference to FIG. 1, FIG. 2, FIG. 3 or FIG. 4.

Parameters used in the operations as shown in FIG. 6A, FIG. 6B, FIG. 6C, FIG. 6D, FIG. 6E, FIG. 6F, FIG. 6G, FIG. 6H or FIG. 6I can be varied to change the structure. For example, during the molding operation as shown in FIG. 6H, a relatively less stress or pressure may result in the semiconductor package structures 1a as described and illustrated with reference to FIG. 1. For example, during the molding operation, a relatively great stress or pressure may result in the semiconductor package structures 1c or 1d as described and illustrated with reference to FIG. 3 or FIG. 4.

For example, during the molding operation as shown in FIG. 6H, part of the film 17 can be spaced apart from the filter structure 13 (e.g. adjacent to periphery of the filter structure 13) due to relatively strong mold flow, which can result in the structure as described and illustrated with reference to FIG. 1C.

For example, during the molding operation as shown in FIG. 6H, part of the film 17 can cover the filter structure 13 (e.g. the side surface of the filter structure 13) due to relatively great stress, which can result in the structure as described and illustrated with reference to FIG. 1D.

In some comparative embodiments, the semiconductor package structures can be manufactured in package level, which is different from the wafer level as discussed above with respect to FIG. 6A FIG. 6B, FIG. 6C, FIG. 6D, FIG. 6E, FIG. 6F, FIG. 6G, FIG. 6H or FIG. 6I. For example, in one comparative embodiment, an electronic device can be disposed on a carrier, and then a lid (with opening) can be disposed on the carrier to cover the electronic device. In order to stop water molecule from entering the lid, a waterproof fabric membrane is disposed on the lid to cover the opening of the lid. Such waterproof fabric membrane generally has a thickness of approximately 300 μm or more, which may inevitably increase thickness of the overall semiconductor package structure. Moreover, the lid also occupies a relatively great area on the carrier, which may adversely affect miniaturization of the semiconductor package structure. Furthermore, manufacture tolerance of the lid, tolerance of placement (+/−100 μm) of the lid, and other parameters can adversely affect performance of the semiconductor package structure. A top surface of the lid can be spaced apart from a top portion of the conductive wire by more than approximately 100 μm.

In some comparative embodiments, a structure similar to the semiconductor package structure 1a as shown in FIG. 1 while the filter structure 13 is eliminated, can be manufactured in a single package level. For example, dam 12 can be formed on a single electronic device 11, then the single electronic device 11 can be bonded and disposed on a single carrier 10, and encapsulant 14 can be formed to encapsulate the electronic device 11, the dam 12 and the carrier 10. A single filter structure 13 can be independently manufactured, can be attached to the dam 12. However, single filter structure 13, which has merely 10 is difficult to handle during manufacturing and can cause significant quantity of damage.

As used herein and not otherwise defined, the terms "substantially," "substantial," "approximately" and "about" are used to describe and account for small variations. When used in conjunction with an event or circumstance, the terms can encompass instances in which the event or circumstance occurs precisely as well as instances in which the event or circumstance occurs to a close approximation. For example, when used in conjunction with a numerical value, the terms can encompass a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. The term "substantially coplanar" can refer to two surfaces within micrometers of lying along a same plane, such as within 40 μm within 30 μm within 20 μm within 10 μm, or within 1 μm of lying along the same plane.

As used herein, the singular terms "a," "an," and "the" may include plural referents unless the context clearly dictates otherwise. In the description of some embodiments, a component provided "on" or "over" another component can encompass cases where the former component is directly on (e.g., in physical contact with) the latter component, as well as cases where one or more intervening components are located between the former component and the latter component.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not necessarily be drawn to scale. There may be distinctions between the artistic renditions in the present disclosure and the actual apparatus due to manufacturing processes and tolerances. There may be other embodiments of the present disclosure which are not specifically illustrated. The specification and the drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations.

What is claimed is:

1. A semiconductor package structure, comprising:
an electronic device having a first surface and an exposed region adjacent to the first surface;
a dam disposed on the first surface and surrounding the exposed region of the electronic device;
a filter structure disposed on the dam, wherein the filter structure comprises a first portion and a second portion surrounding the first portion, and
an encapsulant encapsulating the first surface of the electronic device and surrounding the dam,
wherein a surface of the dam is retracted from a top surface of the encapsulant, wherein the encapsulant has a substantially slant surface or a substantially curve surface, and wherein the encapsulant has an extension on the second portion of the filter structure.

2. The semiconductor package structure of claim 1, wherein the second portion of the filter structure is in direct contact with the dam.

3. The semiconductor package structure of claim 1, wherein the first portion of the filter comprises a mesh from a top view perspective.

4. The semiconductor package structure of claim 1, wherein the first portion of the filter structure defines some cylindrical through holes or some cone-shaped through holes.

5. The semiconductor package structure of claim 1, wherein the second portion of the filter structure has a first thickness adjacent to the first portion of the filter structure and a second thickness away from the first portion of the filter structure, and wherein the first thickness is greater than the second thickness.

6. The semiconductor package structure of claim 1, wherein the dam has a lower portion having a width greater than an upper portion.

7. The semiconductor package structure of claim 1, wherein the dam is retracted from a top surface of the encapsulant.

8. The semiconductor package structure of claim 1, wherein the encapsulant encapsulates the filter structure.

9. The semiconductor package structure of claim 1, further comprising a conductive wire bonded to the first surface of the electronic device, where an upper surface of the dam is disposed at an elevation equal to or greater than a top portion of the conductive wire.

10. The semiconductor package structure of claim 1, wherein the dam overlaps or covers the exposed region of the electronic device.

11. The semiconductor package structure of claim 1, wherein the filter structure has a width less than the electronic device.

12. A semiconductor package structure, comprising:
an encapsulating member having an open cavity defined therein configured to expose an active surface of a semiconductor device;
an filter structure exposed from the open cavity of the encapsulating member, the filter structure including:
a first portion having a plurality of through holes formed therein arranged over the active surface of the semiconductor device, and
a second portion formed around a periphery of the first portion; and
a dam that surrounds the active surface of the semiconductor device and supports the second portion of the filter structure,
wherein the encapsulating member contacts both a lateral surface of the dam and a lateral surface of the filter structure; and
wherein a thickness of the encapsulating member reduces toward an outer edge portion thereof.

13. The structure of claim 12,
wherein in a lateral cross section of the filter structure that shows both of the second portions supported on the dam, the second portions of the filter structure have asymmetric thickness profiles.

* * * * *